United States Patent [19]

Horowitz et al.

[11] 4,434,031

[45] Feb. 28, 1984

[54] METHOD OF ELECTROCATALYTIC OXIDATION OF ORGANIC COMPOUNDS

[75] Inventors: Hugh H. Horowitz, Elizabeth; Harold S. Horowitz, Edison; John M. Longo, New Providence, all of N.J.

[73] Assignee: Exxon Research and Engineering Co., Florham Park, N.J.

[21] Appl. No.: 513,820

[22] Filed: Jul. 15, 1983

Related U.S. Application Data

[63] Continuation of Ser. No. 176,413, Aug. 8, 1980, abandoned.

[51] Int. Cl.³ .......................... C25B 3/02; C25B 11/04
[52] U.S. Cl. ...................................... 204/59 R; 204/78
[58] Field of Search ............. 204/59 R, 78, 79, 290 R, 204/290 F, 291

[56] References Cited

U.S. PATENT DOCUMENTS

| | | | |
|---|---|---|---|
| 4,124,539 | 11/1978 | Horowitz et al. | 252/518 |
| 4,129,525 | 12/1978 | Horowitz et al. | 252/518 |
| 4,146,458 | 3/1979 | Horowitz et al. | 204/277 |
| 4,163,706 | 8/1979 | Horowitz et al. | 204/242 |
| 4,203,871 | 5/1980 | Horowitz et al. | 252/518 |

FOREIGN PATENT DOCUMENTS 2150039 10/1971 Fed. Rep. of Germany .
1415684 11/1975 United Kingdom .

Primary Examiner—F. Edmundson
Attorney, Agent, or Firm—Robert S. Salzman; Joseph J. Dvorak

[57] ABSTRACT

A method for electrocatalytically reacting various oxidizable organic compounds by introducing current by means of an anode into an electrolyte of a cell containing the oxidizable organic compound. The anode comprises an electrocatalyst material which has at least one compound of the formula:

$$A_2[B_{2-x}B'_x]O_{7-y}$$

wherein A is selected from any of the pyrochlore structure metal cations in a group consisting of: Pb, Bi, and Tl, wherein B' is selected from any of the pyrochlore structure metal cations in a group consisting of Pb, Bi, Tl, and Sn; wherein B is a pyrochlore structure metal cation at least a major portion of which is selected from a group consisting of at least one of: Ru, Rh, Ir, and Os, wherein y is equal to or greater than zero and equal to or less than one; and wherein x is equal to or less than one and equal to or greater than zero.

28 Claims, 3 Drawing Figures

RATES OF OXIDATION OF VARIOUS ORGANICS ON LEAD RUTHENATE

V=1.2 VOLTS VS. RHE

METHOD OF ELECTROCATALYTIC OXIDATION OF ORGANIC COMPOUNDS

This is a continuation of application Ser. No. 176,413, filed Aug. 8, 1980, now abandoned.

FIELD OF THE INVENTION

The invention pertains to a method of reacting organic compounds electrocatalytically, and more particularly to a method of electrolytically oxidizing compounds such as alcohols, olefins, and carbonyl compounds, to carboxylates or ketones.

RELATED PATENTS

The following patents are informative for their teachings of electrocatalyst materials and their fabrication. These patents are included herein to serve as a background for the present invention, and also, as these teachings may serve to clarify the present invention, they are meant to be incorporated herein by way of reference.

U.S. Pat. No. 4,203,871 to: Harold S. Horowitz, John M. Longo and Joseph T. Lewandowski, for: "Method of Making Lead and Bismuth Ruthenate and Iridate Phyrochlore Compounds", issued May 20, 1980;

U.S. Pat. No. 4,163,706 to: Harold S. Horowitz, John M. Longo and Joseph T. Lewandowski, for "$Bi_2[M_{2-x}Bi_x]O_{7-y}$ Compounds Wherein M is Ru, Ir or Mixtures Thereof, and Electrochemical Devices Containing Same", issued Aug. 7, 1979;

U.S. Pat. No. 4,146,458 to: Harold S. Horowitz, John M. Longo, and Joel I. Haberman, for: "Electrochemical Device Having an Oxygen Electrode Containing a Pyrochlore-Type Compound Electrocatalyst", issued Mar. 27, 1979;

U.S. Pat. No. 4,129,525, to Harold S. Horowitz, John M. Longo and Joseph T. Lewandowski for: "Method of Making Lead-Rich and Bismuth-Rich Pyrochlore Compounds Using an Alkaline Medium", issued Dec. 12, 1978.

U.S. Pat. No. 4,124,539 to: Harold S. Horowitz, John M. Longo and Joel I. Haberman, for: "$Pb_2[M_{2-x}Pb_x]O_{7-y}$ Compounds Wherein M is Ru, Ir or Mixtures Thereof, and Method of Preparation", issued Nov. 7, 1978.

BACKGROUND OF THE INVENTION

Heretofore it has been taught that pyrochlore structure electrocatalyst materials of the general formula:

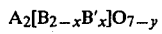

$$A_2[B_{2-x}B'_x]O_{7-y}$$

wherein A is selected from any of the pyrochlore structure metal cations in a group consisting of: Pb, Bi and Tl, wherein B' is selected from any of the pyrochlore structure metal cations in a group consisting of Pb, Bi, Tl, and Sn; wherein B is a pyrochlore structure metal cation at least a major portion of which is selected from a group consisting of at least one of: Ru, Rh, Ir, and Os, wherein y is equal to or greater than zero and equal to or less than one; and wherein x is equal to or less than one and equal to or greater than zero, may be used in the evolution or reduction of oxygen in alkaline solutions. Efforts to explore still other uses for these novel electrocatalyst materials were undertaken when it was noted that they may have ability to change their oxide content or stoichiometry, as a function of potential in alkaline solutions. It was suggested that this behavior might be useful to initiate oxidative reactions of various oxidizable organic compounds.

While it may be argued that the prior art has suggested using pyrochlore electrocatalyst materials for the oxidation of organic substances (see German Application No. 2150039, filed Oct. 7, 1971; and U.K. Patent Specification No. 1,415,684, published Nov. 26, 1975), the electrocatalyst materials of this invention have obtained unique end products through an unusual "reaction selectivity", or "partial oxidation". To better understand what we mean by "reaction selectivity" and "partial oxidation" in terms of this invention, comparison will be made with well known oxygen producing electrocatalyst materials such as platinum. Platinum has been observed to oxidize certain organic compounds to completion and form only carbonates as a reaction end product. This is not a useful result in the context of this invention.

By comparison, the electrocatalyst materials of this invention will catalyze certain organic substances to useful end products such as: carboxylates, carboxylic acids, ketones, etc., in a "partial oxidative" process i.e., a reaction which goes to completion without fully oxidizing the organic reactants.

The new and unexpected reaction products are often observed to be the result of unique reaction pathways or cleavages which as a group of reactions have never before been achieved by electrocatalysis to the best of the inventors' knowledge. It is believed that these uniquely "selective" results are substantially due to the particular and unusual catalytic characteristics of these pyrochlores. The high level of catalytic activity attainable with these materials can be attributed to the high surface area with which they can be fabricated, as taught in the aforementioned U.S. Pat. No. 4,129,525.

BRIEF SUMMARY OF THE INVENTION

In general, the invention relates to a method of electrocatalytically reacting an oxidizable organic compound, comprising the step of introducing current by means of an anode into an electrolyte of a cell containing said organic compound. The anode comprises the electrocatalyst material of this invention which has at least one compound of the formula:

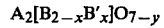

$$A_2[B_{2-x}B'_x]O_{7-y}$$

wherein A is selected from any of the pyrochlore structure metal cations in a group consisting of: Pb, Bi, and Tl, wherein B' is selected from any of the pyrochlore structure metal cations in a group consisting of Pb, Bi, Tl, and Sn; wherein B is a pyrochlore structure metal cation at least a major portion of which is selected from a group consisting of at least one of: Ru, Rh, Ir, and Os, wherein y is equal to or greater than zero and equal to or less than one; and wherein x is equal to or less than one and equal to or greater than zero.

The introduction of current into the electrolyte of the cell is generally made in the voltage range of between 0.3 to 5.0 volts, and more preferably between 0.5 and 1.25 volts relative to a reversible hydrogen electrode in the same electrolyte.

The above method is useful for electrocatalytically generating carboxylates from an organic compound selected from a group consisting of: primary alcohols, olefins, glycols, keto aclohols, diketones, keto acids and hydroxyacids.

The above method has been found to uniquely cleave ketones and secondary alcohols containing at least one alpha hydrogen, where an alkaline electrolyte containing said ketone or secondary alcohol is utilized. That is to say, the carbon-carbon bond next to the oxygen is broken and an acid group is formed on the new terminal carbons.

The above method has also been found to uniquely oxidize secondary alcohols to ketones in a pH range from 2 to 10. For these reactions a bismuth ruthenate or iridate has been found preferable, i.e. A and B' is Bi and B is Ru or Ir.

When olefins are to be cleaved to carboxylic acid, it has been found preferable to use a lead or bismuth ruthenate catalyst, i.e. A and B' are are Pb, or Bi; and B is Ru in the above formula.

For secondary alcohols and ketone cleavages, a lead or bismuth ruthenate catalyst has been found preferable, i.e., A and B' are Pb or Bi, and B is Ru.

Other preferred catalyst materials feature lead and bismuth iridates.

A borate-containing electrolyte ($B_4O_7^=$) with a pH of approximately 9 is preferably used when secondary alcohols are reacted to provide ketones.

In general, the electrolyte may be either aqueous, non-aqueous, or a miscible mixture of aqueous and non-aqueous depending on the reactants or the reaction to be achieved. It is an object of this invention to provide a method of electrocatalytically reacting oxidizable organic compounds with the use of noble metal pyrochlores.

It is another object of the invention to use pyrochlore oxides containing noble metals as catalysts for the electrooxidation of secondary alcohols to ketones in acid or weak alkali electrolytes and the oxidative cleavage of secondary alcohols, ketones and olefinic compounds to carboxylates in strong alkali electrolytes.

These and other objects of this invention will become more apparent and will be better understood with reference to the following detailed description considered in conjunction with the accompanying drawings.

DETAILED DESCRIPTION OF THE INVENTION

The invention features a method of electrocatalytically reacting organic compounds. Current is introduced into a cell having an electrolyte containing the organic compound which is to be reacted. The anode of the cell contains the oxide of a noble metal pyrochlore as defined hereinbefore. The cell also comprises a cathode and means to maintain a potential difference between the cathode and anode. Typically, a reference electrode is also used in order to control the potential of the anode at some precise level relative to the reference. It is advisable, although not absolutely necessary, to provide a separator between the cathode and anode so that hydrogen evolved from the counter electrode may be vented from the cell and, furthermore, so that the oxidized organic products produced at the anode may not come in contact with the cathode and be reduced. The anode is typically immersed in the electrolyte. The organic reactant may be introduced as a liquid or solid which may be solubilized in the electrolyte, or as a liquid which may remain immiscible and is brought into contact with the anode by thorough stirring of the immiscible components. Where the organic is an insoluble solid, it may be reacted as a slurry of fine particles. If the reactant is introduced as a gas, it may be bubbled into the electrolyte or it may be provided to the cell by means of an interface maintaining anode, which consists of a porous, wetproofed electrode that maintains a liquid electrolyte phase on one side and a gaseous reactant phase on the other, simultaneously providing an interface in its interior where electrolyte, gas and catalyst can coexist at a common interface.

Figure 1:
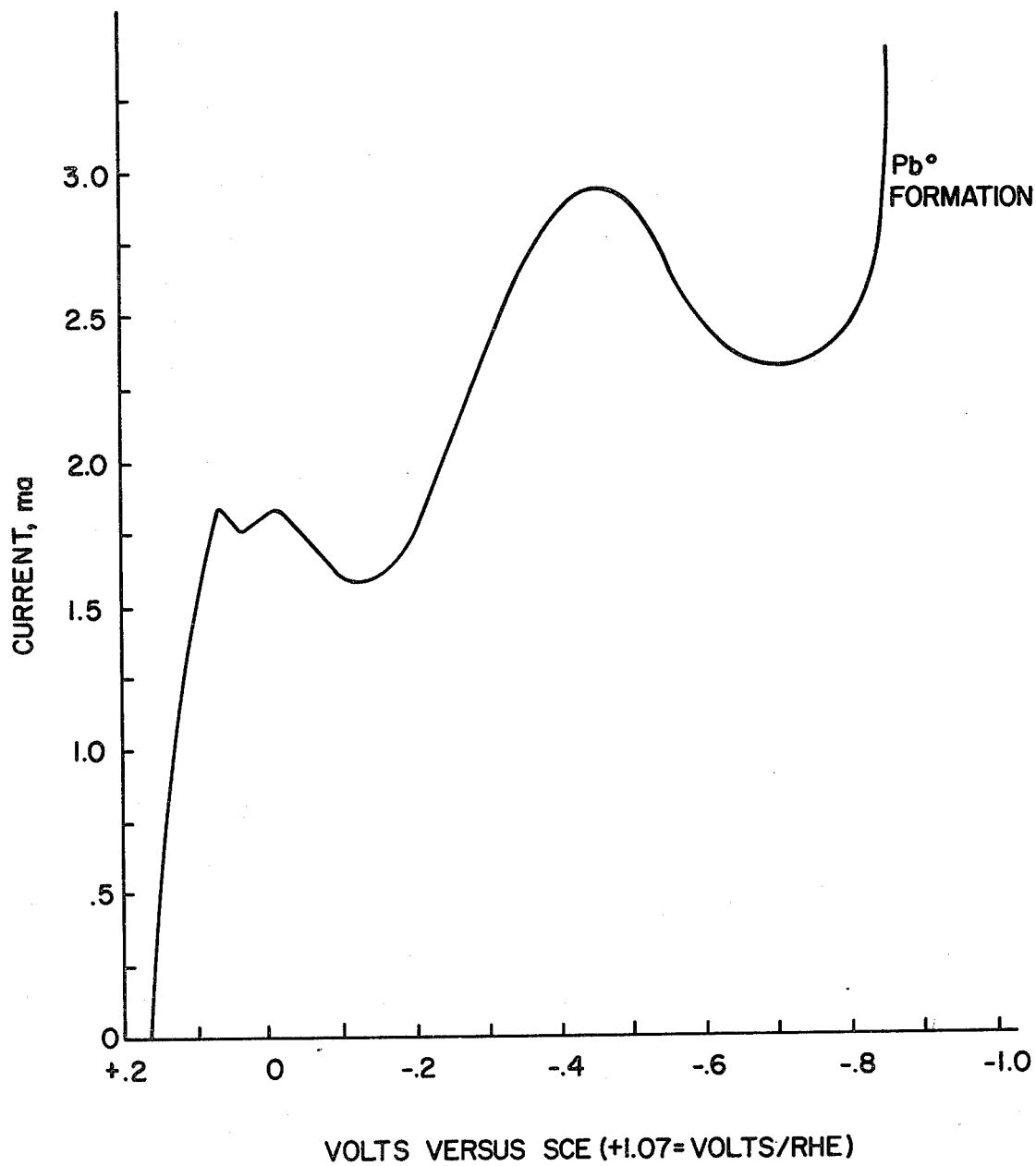
FIG. 1 is a graphical representation of the ability of the pyrochlore crystal structure to undergo oxidative changes as a function of potential in alkaline solution.

Referring to FIG. 1, it is seen that an anode having an oxide of a pyrochlore crystal structure (lead ruthenate) has the ability to undergo oxidative changes as a function of potential in alkaline solutions. This strongly suggests that such materials can electrocatalyze the oxidation of certain substances.

Figure 2:
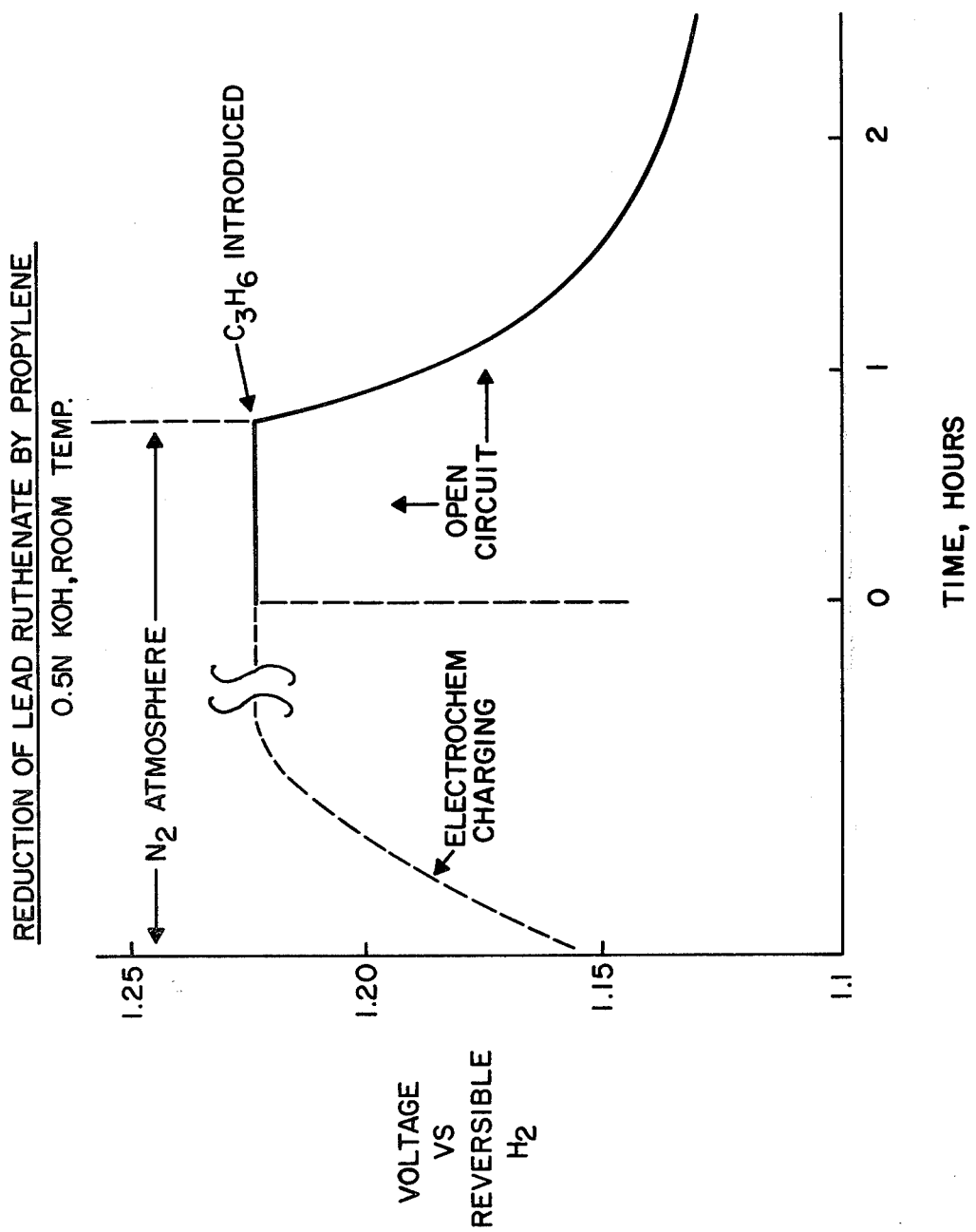
FIG. 2 is a graph illustrating the oxidative capability of a lead ruthenate catalyst.

FIG. 2 further illustrates the oxidative capability of a lead ruthenate anode using propylene in 0.5 N KOH. An electrode containing about 300 mg of high surface area, nonstoichiometric lead ruthenate bonded to an inert gold screen current collector, was potentiostatted under nitrogen at +200 mv vs. saturated calomel (1.22 volts vs. reversible hydrogen in the same electrolyte). This raised its potential to a high level close to the theoretical potential for the reversible oxygen electrode:

  [1]

The cell was "charged" at this potential until all current due to oxide ion incorporation into the lattice decayed to zero:

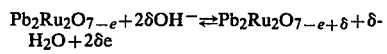  [2]

At this potential the oxygen evolution reaction rate and, therefore, the background current were essentially zero. The electrode was disconnected from the potentiostat and its potential remained unchanged for about an hour.

At time zero, propylene was admitted to the reaction vessel merely by bubbling it through the electrolyte. The potential of the electrode immediately began to drop, leveling off at a lower value (FIG. 2). This means that reaction [2] was reversed because the propylene was oxidized.

Figure 3:
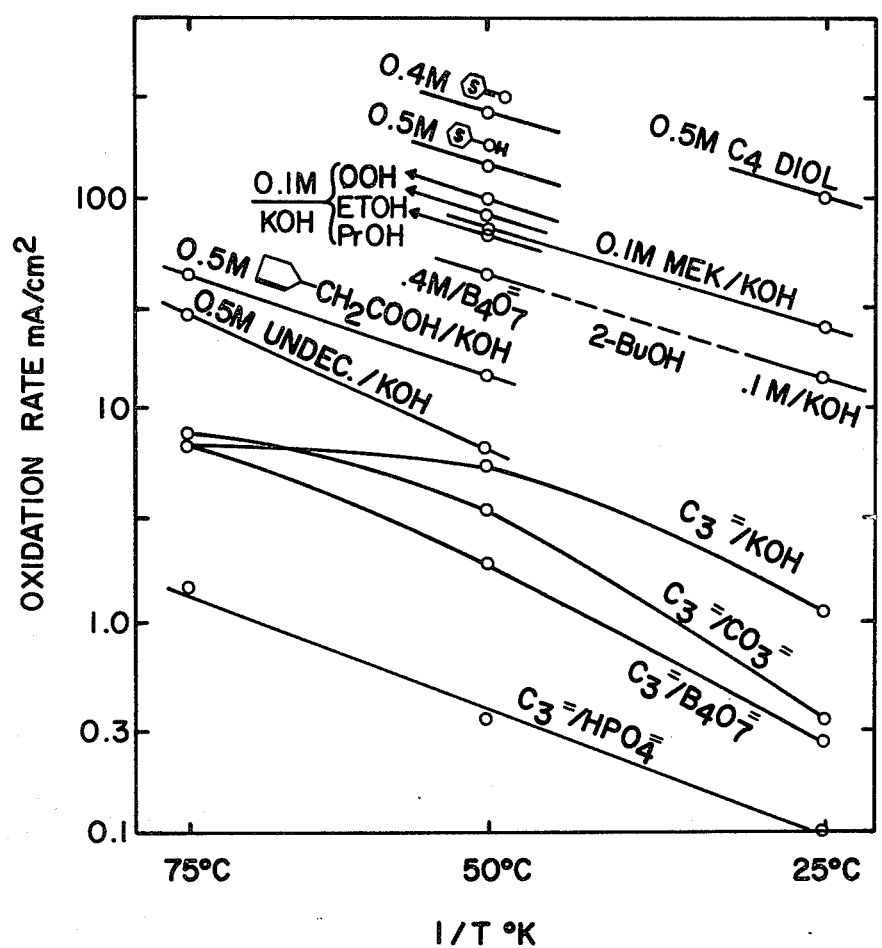
FIG. 3 is a graph depicting the oxidation rate for various electrolyte buffers with respect to temperature.

In borate buffer at pH 9, the oxidation of propylene also occurred, and the selectivity to acetate and $CO_2$, based on the amount of carbonate isolated, was close to 100%. Runs in other buffers showed a tendency for the oxidative rates to decrease with decreasing pH as shown in FIG. 3.

In order to confirm the reactivity and selectivity of the oxidation of isolated double bonds on lead ruthenate with more soluble reactants, two unsaturated carboxylic acids containing a double bond were oxidized which were far removed from the solubilizing carboxylate group. Omega undecylenic acid (11 carbon atoms, double bond next to last carbon) was no more active than propylene at 50° C. but showed increased activity at 75° C.

Oxidations were carried out in aqueous solutions from pH 4.7 to strongly alkaline using a submerged electrode containing the catalyst on an inert gold screen bonded with finely divided polytetrafluoro-ethylene. The reactants were either dissolved in the electrolyte or sparged through it if gaseous.

Table I below summarizes a series of electro-oxidations on a high surface area lead ruthenate catalyst. An olefin, propylene, was cleaved to a carboxylic acid and carbonate with high selectivity (Runs 1 and 2). No electrocatalysts other than the claimed noble metal pyrochlores are known to do this so selectively. Primary alcohols were oxidized to the corresponding carboxylates very selectively, without formation of $CO_2$ due to the further oxidation of the product (Runs 3 and 4).

A secondary alcohol, (secondary butanol) was oxidatively cleaved in alkali to two moles of acetic acid. The expected intermediate, methyl ethyl ketone was also cleaved to the same product as was 2,3 butanediol (Runs 5,6,7 and 8). In weaker alkali however, secondary butanol consumed only 2 electrons/molecule and formed methyl ethyl ketone—no acetate was detected (Run 9).

Similar oxygenate cleavages were demonstrated with cyclohexanol and cyclohexanone, which formed adipic acid (after acidification) (Runs 10 and 11).

Further olefinic cleavages are demonstrated with undecylenic acid which was oxidized to sebacic (+some azelaic) and 2 cyclopentene-1-acetic acid which underwent oxidation to a tricarboxylic acid (Runs 12 and 13).

In Table II below are shown oxidations carried out on bismuth ruthenate. Run 14 illustrates a ketone cleavage while runs 15 and 16 show an olefin cleavage: maleate cleaving to 2 moles of oxalate at pH 4.7 and in strong alkali. Run 17 shows the inactivity of the product oxalate to further oxidation. Sintered nickel, a known catalyst capable of oxidizing primary alcohols, proved to be inert to maleic acid, secondary butanol, and methyl ethyl ketone under the same conditions where lead and bismuth ruthenates were active (Runs 18, 19, 20 and 21). Ruthenium dioxide was also active for the oxidation of methyl ethyl ketone (Run 22) but is not useful because of its tendency to dissolve in alkali as ruthenate ion. Even platinum black (not shown in the tables) does not have the capability of these catalysts. With ethanol in alkali, Pt formed considerable carbonate rather than acetate and deactivated before the substrate was half consumed. With either maleic acid or secondary butanol in alkali, Pt was entirely inactive.

TABLE I

| Run | Sample[1] # | Catalyst | Medium | Temp. °C | Reactant | Products | Selectivity % |
|---|---|---|---|---|---|---|---|
| 1 | 105 | $Pb_2[Ru_{1.66}Pb_{.34}]O_{6.5}$ | 1M KOH | 50 | $C_3H_6$ | $CH_3COO^- + CO_3^=$ | 100 |
| 2 | 81 | $Pb_2[Ru_{1.67}Pb_{.33}]O_{6.5}$ | $Na_2B_4O_7$ | 50 | $C_3H_6$ | $(CH_3COO^-) + CO_3^=$ | ~100 |
| 3 | 90 | " | 1M KOH | 50 | $C_2H_5OH$ | $CH_3COO^-$ | 94 |
| 4 | 103 | $Pb_2[Ru_{1.68}Pb_{.32}]O_{6.5}$ | 1M KOH | 50 | $C_3H_7OH$ | $C_2H_5COO^-$ | ~100 |
| 5 | 112 | $Pb_2[Ru_{1.66}Pb_{.34}]O_{6.5}$ | 1M KOH | 25 | $\eta C_4H_9OH\text{-}2$ | $2CH_3COO^-$ | 67 |
| 6 | 113 | " | 1M KOH | 50 | $\eta C_2H_5CO\text{—}CH_3$ | $2CH_3COO^-$ | 81 |
| 7 | 117 | " | 1M KOH | 50 | $\eta C_4H_9OH\text{-}2$ | $2CH_3COO^-$ | 76 |
| 8 | 121 | " | 2M KOH | 25 | $CH_3(CHOH)_2CH_3$ | $2CH_3COO^-$ | 84 |
| 9 | 128 | " | .125M $Na_2B_4O_7$ | 50 | $C_2H_5CHOH\text{—}CH_3$ | $C_2H_5COCH_3$ | 89 (55*) |
| 10 | 135 | " | 1.5M KOH | 50 | $CH_2\text{—}(CH_2)_4\text{—}CO$ (cyclic) | $(-C_2H_4COO^-)_2$ | 92 |
| 11 | 140 | " | 1.5M KOH | 50 | $CH_2(CH_2)_4CHOH$ (cyclic) | $(-C_2H_4COO^-)_2$ | 89 |
| 12 | 146 | " | 1.5M KOH | 50 | $CH_2=CH-(CH_2)_8COO^-$ | $(-C_4H_8COO^-)_2 + CO_3^=$ | — |
| 13 | 154 | " | 2M KOH | 75 | cyclopentyl-$CH_2\text{—}COO^-$ | cyclopentyl with $-CH_2COO^-$, $-OOCCOO^-$ | 85 |

*Yield low due to evaporation losses.
[1]Notebook #6451

TABLE II

ELECTROORGANIC OXIDATIONS INVOLVING DOUBLE BOND CLEAVAGE

| Run | Sample[1] # | Electrolyte | Catalyst | Potential (mV vs. RHE) | Reactant | Selectivity % |
|---|---|---|---|---|---|---|
| 14 | 111 | 1M KOH | $Bi_2[Ru_{1.25}Bi_{.75}]O_{7-y}$ | 1201 | MEK | 95.6[2] |
| 15 | 124 | 2M KOH | " | 1262 | Maleic Acid | 59.2[3] |
| 16 | 112 | HAc/NaAc pH = 4.7 | $Bi_2[Ru_{1.25}Bi_{.75}]O_{7-y}$ | 1210 | Maleic Acid | Active |
| 17 | 110 | 2M KOH | " | 1222 | Oxalic Acid | Inactive |
| 18 | 106 | 3M KOH | Sintered Ni° | 1408 | Maleic Acid | Inactive |
| 19 | 106 | 3M KOH/75° C. | " | 1394 | Maleic Acid | Inactive |
| 20 | 106 | 3M KOH | " | 1441 | Sec Butanol | Inactive |
| 21 | 106 | 1M KOH | " | 1441 | MEK | Inactive |
| 22 | 108 | 1M KOH | $RuO_2$ | 1241 | MEK | 100[2] |
| 23 | 115 | 1:1 1M KOH/Sulfolane | $Bi_2[Ru_{1.25}Bi_{.75}]O_{7-y}$ | 1250 | Maleic Acid | 66.7[3] |

TABLE II-continued

ELECTROORGANIC OXIDATIONS INVOLVING DOUBLE BOND CLEAVAGE

| Run | Sample[1] # | Electrolyte | Catalyst | Potential (mV vs. RHE) | Reactant | Selectivity % |
|---|---|---|---|---|---|---|
| 24 | 149 | 2M KOH | $Bi_2[Ru_{1.72}Bi_{.28}]O_{7-y}$ | 1216 | Acrylic Acid | 69.8[4] |

[1] Notebook #6483
[2] Product acetate identified by NMR. Amt. determined by titration with HCl. Selectivity based on the reaction:

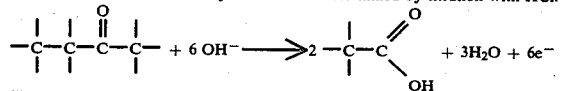

[3] Product oxalate recovered by precipitation with $Ca(NO_3)_2$. Identified by x-ray diffraction and amount determined gravimetrically. Selectivity based on the reaction:

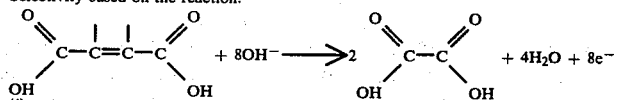

[4] Product oxalate recovered by precipitation with $Ca(NO_3)_2$. Identified by x-ray diffraction and amount determined gravimetrically. Selectivity based on the reaction:

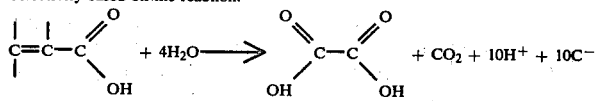

Table III below shows the results of electro-oxidations carried out on ethanol and propanol with various catalysts. It will be seen that high specific surface area is another prerequisite for the activity of the pyrochlore, and that sintered nickel, $RuO_2$ and $NiCo_2O_4$ can match their selectivity whereas other low surface area oxides cannot. A comparison of Table III with Table II shows that whereas several electrocatalysts can promote the oxidation of primary alcohols to carboxylates none can match the unique ability of the noble metal pyrochlores to cleave olefins, secondary alcohols and ketones.

TABLE III

ELECTROORGANIC OXIDATION OF PRIMARY ALCOHOLS

| Run | Sample[1] # | Electrolyte | Catalyst | S.A. | Potential (mV vs. RHE) | Reactant | Selectivity %[2] |
|---|---|---|---|---|---|---|---|
| 24 | 66 | 1M KOH | $Pb_2[Ru_{1.61}Pb_{.39}]O_{7-y}$ | 145 | 1290 | $C_2H_5OH$ | 100 |
| 25 | 72 | 1M KOH | $Pb_2Ru_2O_{6.5}$ | 3.3 | 1290 | $C_2H_5OH$ | 98.5 |
| 26 | 74 | 1M KOH | $Bi_2Ru_2O_7$ | 0.2 | 1440 | $C_2H_5OH$ | Inactive |
| 27 | 67 | 1M KOH | $Bi_2[Ru_{1.46}Bi_{.54}]O_{7-y}$ | 157 | 1220 | $C_2H_5OH$ | 100 |
| 28 | 105 | 1M KOH | " | " | 1221 | $C_3H_7OH$ | 99.4 |
| 29 | 89 | HAc/NaAc pH = 4.7 | " | " | 1210 | $C_3H_7OH$ | Active for propionate-Selectivity not determined |
| 30 | 75 | 1M KOH | $PbO_2$ | 0.3 | 1440 | $C_2H_5OH$ | Inactive |
| 31 | 76 | 1M KOH | $RuO_2$ | 14 | 1240 | $C_2H_5OH$ | 100 |
| 32 | 93 | 1M KOH | $RuO_x$ | 145 | 1240 | $C_2H_5OH$ | Unstable |
| 33 | 87 | 1M KOH | $BaPbO_3$ | 0.8 | 1440 | $C_2H_5OH$ | Inactive |
| 34 | 97 | 1M KOH | Sintered Ni° |  | 1440 | $C_2H_5OH$ | 98.2 |
| 35 | 100 | 1M KOH | $NiCo_2O_4$ | 64 | 1240 | $C_2H_5OH$ | 97.3 |

[1] Notebook #6483 All oxidations carried out at 50° C.
[2] Product in each case was the corresponding carboxylic acid. Amt. determined by titration with HCl. Identified by NMR. Selectivity calculated on the basis of a 4 electron oxidation of the alcohol to the carboxylic acid.

In addition to acidic and basic aqueous electrolytes, these pyrochlores can be used as electro-oxidation catalysts in electrolytes containing a significant organic component. This is important to aid the solubility of organic reactants. Maleic acid is found to be very reactive in a 1:1 m KOH/sulfolane electrolyte as shown in Run 23—Table II.

The use of "expanded" noble metal pyrochlores which have varying amounts of lead and bismuth replacing the noble metal are particularly well suited for the electro-oxidation of organics. This is because they can be prepared with the highest surface area of all pyrochlores. Other advantages of this class of materials are their high electrical conductivity, range of oxygen nonstoichiometry and lower noble metal content per unit activity.

Having thus described the invention, what is desired to be protected by Letters Patent is presented in the following appended claims.

What is claimed is:

1. A method of electrocatalytically, partially oxidizing an oxidizable organic compound comprising the step of introducing current by means of an anode into an electrolyte of a cell containing said oxidizable organic compound, said anode comprising an electrocatalyst material having at least one compound of the formula:

wherein A is selected from any of the pyrochlore structure metal cations in a group consisting of: Pb, Bi, and Tl, wherein B' is selected from any of the pyrochlore structure metal cations in a group consisting of Pb, Bi, Tl, and Sn; wherein B is a pyrochlore structure metal cation at least a major portion of which is selected from a group consisting of at least one of: Ru, Rh, Ir, and Os, wherein Y is equal to or greater than zero and equal to or less than one; and wherein x is equal to or less than one and equal to or greater than zero, said electrolyte of said cell being selected from aqueous solutions, non-aqueous solutions and mixtures of aqueous and non-aqueous solutions and said current being introduced into said electrolyte of said cell at a voltage range between 0.5 and 1.25 volts when said electrolyte is an aqueous solution and between 0.5 and 3.0 volts when said electrolyte is a non-aqueous solution or a mixture of aqueous and non-aqueous solutions, said voltage being relative to the reversible hydrogen potential in the same electrolyte whereby said organic compound is partially oxidized.

2. The method of claim 1, wherein A and B' are preferably Pb.

3. The method of claim 1, wherein A and B' are preferably Bi.

4. The method of claim 2, wherein B is preferably Ru.

5. The method of claim 3, wherein B is preferably Ru.

6. The method of claim 2, wherein B is preferably Ir.

7. The method of claim 3, wherein B is preferably Ir.

8. A method of electrocatalytically generating carboxylates from oxidizable compounds selected from a group consisting of: primary alcohols, olefins, glycols, keto alcohols, diketones, ketoacids, and hydroxyacids, comprising the step of introducing current by means of an anode into an electrolyte of a cell containing at least one of said oxidizable compounds, said anode comprising an electrocatalyst material having at least one compound of the formula:

$$A_2[B_{2-x}B'_x]O_{7-y}$$

wherein A is selected from any of the pyrochlore structure metal cations in a group consisting of: Pb, Bi, and Tl, wherein B' is selected from any of the pyrochlore structure metal cations in a group consisting of Pb, Bi, Tl, and Sn; wherein B is a pyrochlore structure metal cation at least a major portion of which is selected from a group consisting of at least one of: Ru, Rh, Ir, and Os, wherein y is equal to or greater than zero and equal to or less than one; and wherein x is equal to or less than one and equal to or greater than zero, said electrolyte of said cell being selected from aqueous solutions, non-aqueous solutions and mixtures of aqueous and non-aqueous solutions and said current being introduced into said electrolyte of said cell at a voltage range between 0.5 and 1.25 volts when said electrolyte is an aqueous solution and between 0.5 and 3.0 volts when said electrolyte is a non-aqueous solution or a mixture of aqueous and non-aqueous solution, said voltage being relative to the reversible hydrogen potential in the same electrolyte whereby carboxylates are generated.

9. The method of claim 8, wherein A and B' are preferably Pb.

10. The method of claim 8, wherein A and B' are preferably Bi.

11. The method of claim 10, wherein B is preferably Ru.

12. The method of claim 11, wherein B is preferably Ru.

13. The method of claim 10, wherein B is preferably Ir.

14. The method of claim 11, wherein B is preferably Ir.

15. A method of electrocatalytically cleaving ketones and secondary alcohols containing at least one alpha hydrogen to form carboxylates, comprising the step of introducing current by means of an anode into an alkaline electrolyte of a cell containing said ketone or secondary alcohol, said anode comprising an electrocatalyst material having at least one compound of the formula:

$$A_2[B_{2-x}B'_x]O_{7-y}$$

wherein A is selected from any of the pyrochlore structure metal cations in a group consisting of: Pb, Bi and Tl, wherein B' is selected from any of the pyrochlore structure metal cations in a group consisting of Pb, Bi, Tl, and Sn, wherein B is pyrochlore structure metal cation at least a major portion of which is selected from a group consisting of at least one of: Ru, Rh, Ir, and Os, wherein y is equal to or greater than zero and equal to or less than one; and wherein x is equal to or less than one and equal to or greater than zero, said electrolyte of said cell being selected from aqueous solutions, non-aqueous solutions and mixtures of aqueous and non-aqueous solutions and said current being introduced into said electrolyte of said cell at a voltage range between 0.5 and 1.25 volts when said electrolyte is an aqueous solution and between 0.5 and 3.0 volts when said electrolyte is a non-aqueous solution or a mixture of aqueous and non-aqueous solutions, said voltage being relative to the reversible hydrogen potential in the same electrolyte whereby carboxylates are formed.

16. The method of claim 15, wherein A and B are preferably Pb.

17. The method of claim 15, wherein A and B are preferably Bi.

18. The method of claim 16, wherein B is preferably Ru.

19. The method of claim 17, wherein B is preferably Ru.

20. The method of claim 16, wherein B is preferably Ir.

21. The method of claim 17, wherein B is preferably Ir.

22. The method of claim 15, wherein said electrolyte is an aqueous, alkaline solution of approximate pH greater than 9.

23. The method of claim 15, wherein said electrolyte is a mixture of aqueous alkaline and non-aqueous solvents.

24. A method of electrocatalytically, partially oxidizing secondary alcohols to ketones in a pH range from 2 to 10, comprising the step of introducing current by means of an anode into an electrolyte of a cell containing an oxidizable secondary alcohol, said anode comprising an electrocatalyst material having at least one compound of the formula:

$$A_2[B_{2-x}B'_x]O_{7-y}$$

wherein A is selected from any of the pyrochlore structure metal cations in a group consisting of: Pb, Bi, and Tl, wherein B' is selected from any of the pyrochlore structure metal cations in a group consisting of Pb, Bi, Tl, and Sn; wherein B is a pyrochlore structure metal cation at least a major portion of which is selected from a group consisting of at least one of: Ru, Rh, Ir and Os, wherein y is equal to or greater than zero and equal to or less than one; and wherein x is equal to or less than one and equal to or greater than zero, said electrolyte of said cell being selected from aqueous solutions, non-aqueous solutions and mixtures of aqueous and non-aqueous solutions and said current being introduced into said electrolyte of said cell at a voltage range between 0.5 and 1.25 volts when said electrolyte is an aqueous solution and between 0.5 and 3.0 volts when said electrolyte is a non-aqueous solution or a mixture of aqueous and non-aqueous solutions, said voltage being relative to the reversible hydrogen potential in the same electrolyte whereby said secondary alcohol is partially oxidized to ketones.

25. The method of claim 24, wherein the preferred electrolyte contains a borate ($B_4O_7^=$) at a pH of approximately 9.00.

26. The method of claim 24, wherein A and B' are preferably Bi, and B is Ru.

27. The method of claim 24, wherein A and B' are preferably Bi, and B is Ir.

28. The method of claim 24, wherein said electrolyte consists of a mixture of non-oxidizable, non-aqueous, and aqueous acidic solutions.

* * * * *